(12) United States Patent
Williams, Jr. et al.

(10) Patent No.: US 7,806,850 B2
(45) Date of Patent: Oct. 5, 2010

(54) INSUFFLATING SYSTEM, METHOD, AND COMPUTER PROGRAM PRODUCT FOR CONTROLLING THE SUPPLY OF A DISTENDING MEDIA TO AN ENDOSCOPIC DEVICE

(75) Inventors: Robert C. Williams, Jr., Fort Salonga, NY (US); Peter M. Kurzyna, Glenmoore, PA (US); Kenneth E. Wolcott, Centerport, NY (US); Jeffrey B. Cushner, Woodmere, NY (US)

(73) Assignee: Bracco Diagnostics Inc., Princeton, NJ (US)

( * ) Notice: Subject to any disclaimer, the term of this patent is extended or adjusted under 35 U.S.C. 154(b) by 602 days.

(21) Appl. No.: 11/257,229

(22) Filed: Oct. 24, 2005

(65) Prior Publication Data

US 2007/0106209 A1    May 10, 2007

(51) Int. Cl.
*A61M 37/00* (2006.01)
*A61M 31/00* (2006.01)

(52) U.S. Cl. .......................................... 604/26; 604/66
(58) Field of Classification Search .................. 604/23, 604/26, 30, 31, 104, 106, 65–67; 606/191, 606/192
See application file for complete search history.

(56) References Cited

U.S. PATENT DOCUMENTS

| | | | |
|---|---|---|---|
| 5,006,109 A * | 4/1991 | Douglas et al. | 604/26 |
| 5,176,629 A * | 1/1993 | Kullas et al. | 604/31 |
| 5,178,606 A * | 1/1993 | Ognier et al. | 604/31 |
| 5,328,458 A * | 7/1994 | Sekino et al. | 604/23 |
| 5,549,546 A * | 8/1996 | Schneider et al. | 604/26 |
| 6,866,654 B2 * | 3/2005 | Callan et al. | 604/247 |

OTHER PUBLICATIONS

The International Search Report for PCT Application No. PCT/US2006/041291, completed Jul. 31, 2007, mailed Sep. 13, 2007.

* cited by examiner

*Primary Examiner*—Kevin C Sirmons
*Assistant Examiner*—Bradley J Osinski
(74) *Attorney, Agent, or Firm*—Alston & Bird LLP

(57) ABSTRACT

The present invention is directed to a system, method, and computer program product for controlling the supply of a distending media (such as an insufflating gas) from a distending media source to an endoscopic device so as to prevent the excess venting and/or waste of distending media. More specifically the present invention provides for the detection of a pressure level within a lumen of an endoscopic device and adjusts a supply parameter of the distending media based at least in part on the detected pressure level, and in some cases on the relationship between the detected pressure level and a user-defined threshold.

27 Claims, 9 Drawing Sheets

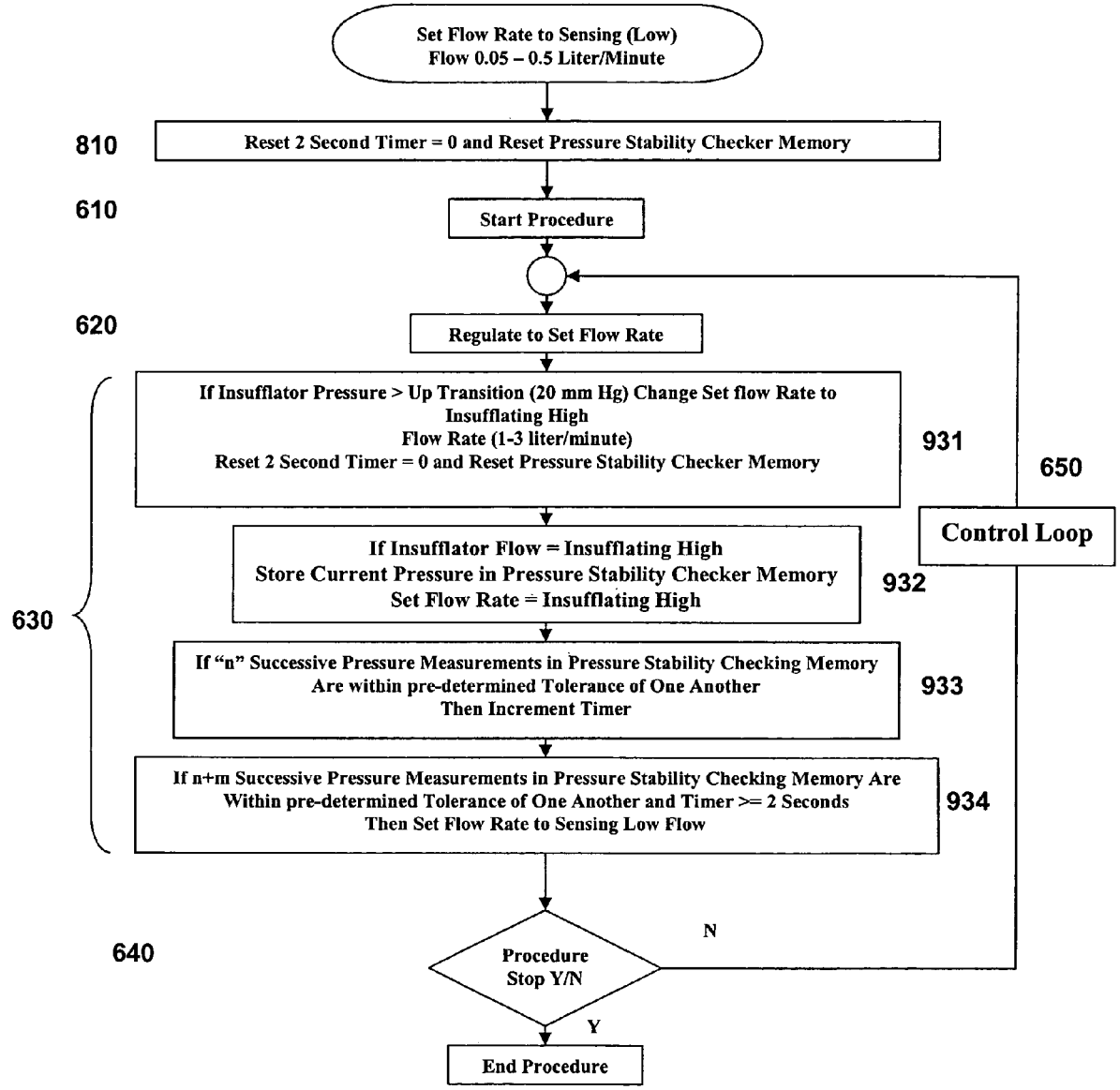

INSUFFLATING SYSTEM, METHOD, AND COMPUTER PROGRAM PRODUCT FOR CONTROLLING THE SUPPLY OF A DISTENDING MEDIA TO AN ENDOSCOPIC DEVICE

FIELD OF THE INVENTION

The present invention relates generally to gas insufflating devices often used in endoscopic medical procedures to selectively distend one or more cavities defined within a subject's anatomy. More particularly the present invention relates to a system, method, and/or computer program product for providing more precise electro-pneumatic control over the supply of insufflating gas provided to an insufflating device during a medical procedure such that the insufflating gas may be better conserved.

BACKGROUND OF THE INVENTION

In the current practice of gastrointestinal (GI) endoscopy, ambient room air is predominantly used as a gaseous media for distending some portion of the GI tract when performing this procedure. Within the practice of medicine, it is widely known that when distending the GI tract (or other body cavities, such as in the case of laparoscopy) with ambient room air, the constituent nitrogen gas found in ambient room air is not readily remediated through normal metabolic and respiratory process. Thus, post medical procedure, gas pockets of nitrogen are not easily tolerated by the human body and lead to post-procedure pain and discomfort until they resolve themselves. Similarly, oxygen found in ambient room air is also not as easily absorbed. Carbon dioxide ($CO_2$), on the other hand, may be very quickly absorbed and expelled via normal respiration post-procedure by an individual undergoing a medical procedure wherein the distention of a body cavity by insufflation is required. As one skilled in the art will appreciate, it is common to use $CO_2$ insufflation (via the use of an electro-pneumatic insufflator) for medical procedures involving abdominal or gynecological laparoscopy and more recently virtual colonoscopy. For these medical procedures, closed anatomical cavities are distended (much like a balloon) with an electro-pneumatic insufflator. The electro-pneumatic insufflators utilized in such procedures delivers $CO_2$ through a trocar, entry needle, or catheter at a constant regulated flow rate until a selected pressure is reached to maintain the desired level of distention for the duration of the medical procedure. Should there be any leakage or absorption of $CO_2$ during laparoscopic or virtual colonoscopy procedure, the electro-pneumatic insufflator makes up for the shortfall by delivering the additional $CO_2$ to maintain the set distention pressure.

However, in medical procedures utilizing an endoscope for gastrointestinal endoscopy, distention media air passes through lumens of the endoscope to the patient's GI tract. Such distention of the GI tract using current equipment typically involves the physician performing the procedure wherein a port or valve on the control section of the endoscope is manually manipulated by the physician over the course of the procedure to achieve the desired level of distention. Unlike laparoscopic and virtual colonoscopy procedures, the distention media is not automatically delivered at a specified flow rate until the anatomic cavity reaches a specified pressure or level of distention where thereafter it is maintained in equilibrium at a set pressure. For GI endoscopy, GI tract insufflation is typically localized to support navigation of the endoscope and perform any evaluation or distal end articulated procedures through the scope. Additionally, supporting the use of the endoscope, irrigation and suction features are also frequently used. Thus, in current systems and methods for GI endoscopy, the distention gas (ambient room air) is supplied to the endoscope at a continuous flow rate with a maximum source pressure well in excess of the clinical requirements for laparoscopy and virtual colonoscopy. Through manipulation of the endoscope controls (including, in most cases a bypass vent valve), excess distention gas that is not directed through the endoscope to the patient is bypassed to atmosphere. Currently available endoscopy light sources have simple diaphragm compressor pumps integrated therein to supply room air as a distention media through the lumens of the endoscope. In this scenario, there is no accounting for any specific volume of air and the pump typically runs continuously for the duration of the procedure.

There are also rudimentary $CO_2$ insufflation support devices that are currently marketed for endoscopy procedures. However, these are non-electronic devices that consist of a pressure regulator and flow restrictor in series with a bottled gas source (such as a $CO_2$ tank) that mimic the equivalent flow and pressure output as that of the ambient room air compressor in the endoscope light source. Furthermore, such existing $CO_2$ insufflation support devices have the disadvantage of continually discharging $CO_2$ into the surrounding atmosphere whereby ventilation adequacy may be of concern. Furthermore existing $CO_2$ insufflation support devices may also quickly deplete $CO_2$ supplies by continuously venting unused $CO_2$ to the procedure room and thus may require frequent changing of the $CO_2$ supply cylinders in fluid communication therewith.

Thus, there exists a need for a system, method, and/or computer program product for precisely controlling the flow of insufflating gas (such as $CO_2$) to a GI endoscope in response to detected pressure changes that may be associated with a physician's control inputs to a control portion of the GI endoscope. In addition, there exists a need for a system and method for automatically adjusting the flow rate between a "standby" $CO_2$ conservation mode (characterized by a low flow rate) to a clinically-active insufflation mode (characterized by a higher flow rate) with no intervention on the part of the user except for the normal control inputs to the endoscope. There also exists a need for a computer program product for controlling an electro-pneumatic insufflator, such that a user may input insufflation gas control parameters in order to optimize the control of insufflating gas for a selected procedure.

SUMMARY OF THE INVENTION

The various system, method, and computer program product embodiments of the present invention satisfy the needs listed above and provide other advantages as described below. In at least one alternative embodiment, the present invention provides an insufflating system adapted to be in fluid communication with a source of a distending media and an endoscopic device so as to deliver the distending media to the endoscopic device. According to one embodiment the insufflating system comprises a controller for detecting a pressure level within a lumen of the endoscopic device and a valve assembly in communication with the controller and in fluid communication between the source of distending media and the endoscopic device. Thus, the valve assembly may be capable of delivering the distending media to the endoscopic device and adjusting a flow rate of the distending media delivered to the endoscopic device in response to the detected pressure level so as to prevent excess supply and waste of the distending media. For example, a detected high pressure level in the lumen of the endoscopic assembly may be indicative of the delivery of distending media to a patient, while a detected low pressure level may be indicative of the venting of distending media to the procedure room. Thus, the insufflating system embodiments of the present invention may quickly and efficiently adjust the flow rate of distending media in response to these detected pressure levels so as to prevent the excess venting of distending media to the ambient environment.

Furthermore, according to some alternative embodiments of the insufflating system of the present invention, the insufflating system may also comprise a disposable tubing set in fluid communication between an output of said valve assembly and the lumen of the endoscopic device, and/or a filter device in fluid communication between an output of said valve assembly and a lumen of the endoscopic device. The filter device may comprise at least one of a biological filter and a hydrophobic filter so as to prevent the passage of a pathogen from the endoscopic device to the valve assembly of the insufflating system. According to some system embodiments of the present invention, the controller may comprise a pressure transducer for detecting a pressure level within a lumen of the endoscopic device. Furthermore, according to some embodiments, the valve assembly may comprise an electro-pneumatic valve in communication with the controller for controlling a flow rate of the distending media. In addition, according to various embodiments, the distending media delivered by the insufflating system may comprise at least one of: carbon dioxide; anti-spasmodic gaseous media; relaxant gaseous media; and/or combinations of such media.

Some insufflating system embodiments of the present invention may also comprise a user interface, in communication with said controller and said valve assembly, for receiving a user input so as to set operating parameters for the insufflating system. According to some system embodiments, the user interface may also comprise a display for displaying data including, but not limited to: a volume of distending media delivered to the endoscopic device; a volume of distending media remaining in the distending media source; an indication of the user input; and combinations thereof.

In some system embodiments, the user input may comprise at least one pressure threshold. According to such embodiments, the controller may control the valve assembly to adjust the flow rate to a relatively high insufflating flow rate if the detected pressure is greater than the at least one pressure threshold. Furthermore, the controller may be further adapted to control the valve assembly to adjust the flow rate to a relatively low sensing flow rate if the detected pressure is less than the at least one pressure threshold, so as to conserve distending media when the pressure level indicates that insufflating media is being vented to the environment. For example, according to various system embodiments, the (high) insufflating flow rate may be between about 1 and 20 liters per minute and the (low) sensing flow rate may be between about 0.05 and 0.5 liters per minute.

According to another example wherein the insufflating system comprises a user interface, the user input may comprise both a low pressure transition point and a high pressure transition point. In some such embodiments, the controller may control the valve assembly to adjust the flow rate from a sensing flow rate to an insufflating flow rate if the detected pressure rises above the low pressure transition point. Furthermore, the controller may also control the valve assembly to adjust the flow rate from the insufflating flow rate to the sensing flow rate if the detected pressure falls below the high pressure transition point. The use of these two pressure transition points may thus improve the system performance and response characteristics by eliminating the pneumatic latency sometimes associated with a single pressure threshold.

In some system embodiments of the present invention, the controller may comprise a programmed time limit to minimize erroneous and/or unintended changes between sensing and insufflating flow rates. For example, the controller may control the valve assembly to adjust the flow rate from a (low) sensing flow rate to a (high) insufflating flow rate only when the detected pressure rises above the low pressure transition point for a time period exceeding the time threshold. Furthermore, the controller may control the valve assembly adjust the flow rate from the insufflating flow rate to the (relatively low) sensing flow rate only when the detected pressure falls below the high pressure transition point for a time period exceeding the time limit. Thus, if a clinician's inputs to control the endoscopic device periodically cause short pressure drops, the system will not prematurely shift the delivery of distending media to the low sensing flow rate that is used to conserve distending media.

Furthermore, according to some embodiments, the insufflating system may adaptively "learn" to apply appropriate low and high pressure thresholds and time limits automatically using stored detected pressure data. For example, some such system embodiments may comprise a memory device in communication with the controller for storing data comprising detected pressures for a plurality of insufflating procedures. The controller may further automatically define a time limit, a low pressure transition point, and a high pressure transition point such that the controller may appropriately control the valve assembly using the rules set forth above in order to conserve distending media when the detected pressure levels in the endoscope indicate that insufflating flow rates may not be required.

The present invention also provides various method and computer program embodiments for delivering distending media to an endoscopic device in fluid communication with a source of a distending media. The methods and computer program products may comprise, in some embodiments, detecting a pressure level within a lumen of the endoscopic device; delivering the distending media to the endoscopic device; and adjusting a flow rate of the distending media delivered to the endoscopic device in response to the detected pressure level so as to prevent the excess supply and waste of the distending media. The method and computer program product embodiments of the present invention may also comprise filtering a fluid pathway between the source and the endoscopic device so as to prevent passage of a pathogen from the endoscopic device to the source of the distending media. Other embodiments may also comprise receiving a user input for controlling the adjusting step.

In some method and computer program embodiments, the received user input may comprise at least one pressure threshold. In such embodiments, the adjusting step recited above may further comprise adjusting the flow rate to a relatively high insufflating flow rate if the detected pressure is greater than the at least one pressure threshold and adjusting the flow rate to a relatively low sensing flow rate if the detected pressure is less than the at least one pressure threshold. For example, as described above with respect to the system embodiments, the insufflating flow rate may be between about 1 and 20 liters per minute and the sensing flow rate may be between about 0.05 and 0.5 liters per minute.

According to other method and computer program products, the user input received in the receiving step may comprise both a low pressure transition point and a high pressure transition point. In some such embodiments, the adjusting step may further comprise adjusting the flow rate from a sensing flow rate to an insufflating flow rate if the detected pressure rises above the low pressure transition point and adjusting the flow rate from the insufflating flow rate to the sensing flow rate if the detected pressure falls below the high pressure transition point. In other method and computer program product embodiments wherein a time limit is provided, the adjusting step may also comprise adjusting the flow rate from a sensing flow rate to an insufflating flow rate only if the detected pressure rises above the low pressure transition point for a time period exceeding the time limit and adjusting the delivery parameter from the insufflating flow rate to the sensing flow rate only if the detected pressure falls below the high pressure transition point for a time period exceeding the time limit. In such embodiments, the time limit may ensure that the method and computer program product embodiments do not provide flow rate adjustments that overreact to temporary and/or aberrant pressure rises and/or drops that are not indicative of a change in the required distending media flow rate.

Some other method and computer program embodiments may provide for adaptive responses to detected pressures stored over the course of multiple endoscopic procedures. For example, method embodiments may comprise storing data comprising a plurality of detected pressure profiles corresponding to a plurality of insufflating procedures and defining a time limit, a low pressure transition point, and a high pressure transition point, at least partially based on the stored data. According to some such embodiments, the adjusting step may further comprises adjusting the flow rate from a sensing flow rate to an insufflating flow rate if the detected pressure rises above the low pressure transition point for a time period exceeding the time limit and adjusting the flow rate from the insufflating flow rate to the sensing flow rate if the detected pressure falls below the high pressure transition point for a time period exceeding the time limit.

Such embodiments provide significant advantages as described and otherwise discussed herein.

BRIEF DESCRIPTION OF THE DRAWINGS

Reference will now be made to the accompanying drawings, which are not necessarily drawn to scale. The drawings are for illustrative purposes only, and are not intended to limit the scope of the present invention.

FIG. 9 shows a non-limiting flow diagram of an adaptive method and/or computer program embodiment of the present invention including pressure detecting, delivery, and flow rate adjusting steps, wherein the adjusting step comprises adjusting a flow rate in response to the relative value of a detected pressure with respect to several automatically determined threshold values including: a low pressure transition point; a high pressure transition point; and a time limit.

DETAILED DESCRIPTION OF THE INVENTION

Figure 1:
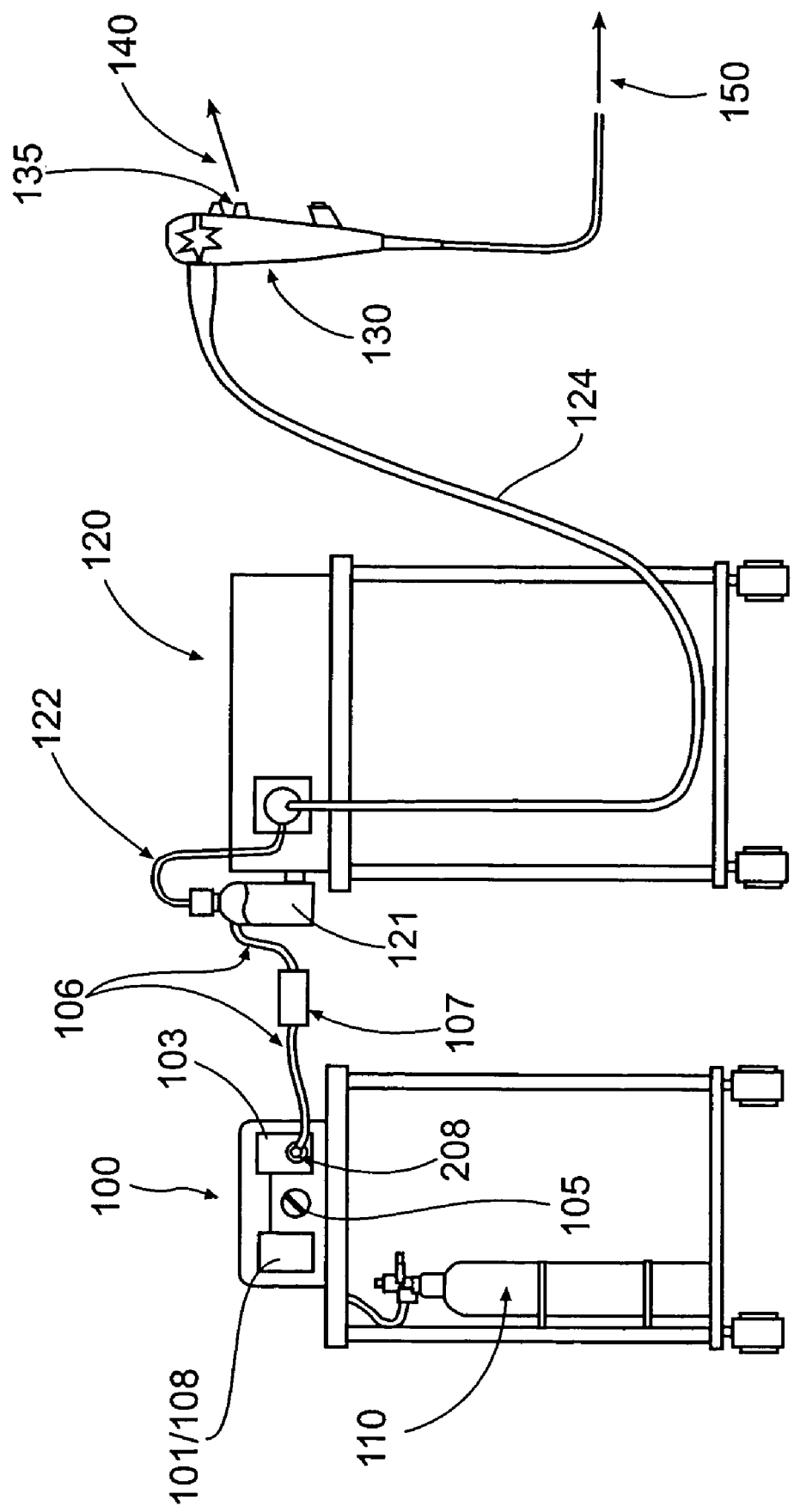
FIG. 1 shows a non-limiting schematic of an insufflating system in fluid communication between a source of distending media and an endoscopic device according to one embodiment of the present invention.

The present invention will be described with reference to the accompanying drawings, where applicable. It is understood that the present invention may be embodied in many different forms and should not be construed as limited to the embodiments set forth herein; rather, these embodiments are provided for illustrative purposes only. Like numbers refer to like elements throughout.

While the embodiments of the system, method, and computer program product for delivering distending media to an endoscopic device are described below in the context of providing insufflating media comprising carbon dioxide for an endoscopic procedure (such as a colonoscopy), it should be understood that the embodiments of the present invention may also be utilized to provide a precisely controllable supply of distending media of various types (including various gas mixtures and media containing relaxants and/or non-spasmodic agents) to a variety of different endoscopic and/or laparoscopic instruments requiring a supply of distending media.

As described herein, the terms "endoscope" and "endoscopic device" refers to both an endoscope 130 (including a control portion 135 thereof) and a light source unit 120 operably engaged therewith, forming the components of a conventional endoscopic system.

As one skilled in the art will appreciate, the conventional practice for gastrointestinal endoscopy involves the connection of an endoscope 130 to a light source unit 120. This arrangement is shown generally in FIG. 1. The endoscope 130 is the portion of the system which the clinician actively manipulates while navigating through the anatomic cavity under evaluation. The distal end of the endoscope 130 may comprise a variety of components and lumens, including but not limited to: an illumination fiber optic bundle, imaging optics, an irrigation lumen, an insufflation lumen 150 and/or other utility lumens. A mid section of the endoscope 130 may include a control section 135 whereby an operator of the endoscope may control articulation, irrigation, insufflation and other endoscope 130 functions. At the proximal end of the endoscope 130, the endoscope may be operably engaged with the light source unit 120. The light source 120 portion of the system can provide several functions including but not limited to: providing a fiber optic light source; providing objective optics with video or digital image conversion; providing an internal air compressor for insufflation and irrigation; and providing irrigation & irrigation connection via a "water bottle" 121.

Conventional air insufflation for delivering distending media during endoscopic procedures utilizes an air compressor that may be internal to the light source 120. During use, an air pump or compressor (not shown) inside of the light source 120 may be turned on and in most cases the air pump operates continuously for the duration of an endoscopic procedure. The flow of compressed air may proceed from the light source 120 through a lumen 124 of the endoscope 130. Room air moved by the air pump flows through the lumen 124 to the control section 135 of the endoscope. One skilled in the art will appreciate that the endoscope 130 may comprise an air/water valve operably engaged with the control section 135 which may be used to regulate gas by the clinician down through the remainder of the endoscope to the patient (see, the insufflating flow pathway 150). For most endoscope 130 configurations, the portion of the air/water valve that regulates the insufflation air to the patient (see element 150) is simply an open port in the control portion 135 of the endoscope 130. During operation, insufflation air from the continuously running air pump is either vented to atmosphere or diverted through the endoscope to the patient (see element 150, showing the insufflating flow pathway) by the clinician selectively placing a finger over the port provided as part of the air/water valve of the endoscope 130 as required.

Conventional endoscopes 130 also include an irrigation lumen such that insufflation air from the air pump is also branched into the water bottle 121 through a lumen 122. The insufflation air from the air pump acts as the pressurizing medium for the water in the water bottle 121. Should an operator of the endoscope choose to deliver water through the distal end 150 of the endoscope 130 for irrigation or imaging optics clearing, the clinician may simply place a finger over the port on the air/water valve and depress it inward to open a flow path from the water bottle 121. In this case, irrigating water instead of insufflating air is diverted to the patient through a parallel irrigation lumen. Pressure generated by the air pump may displace water from the water bottle 121 through the endoscope 130. As in the case of the insufflating air, the irrigating water is selectively administered to the patient via the hand-operated port on the control section 135 of the endoscope 130.

FIG. 1 shows an insufflating system 100, according to one embodiment of the present invention, in fluid communication with a source 110 of a distending media (such as a bottle of insufflating gas) and an endoscopic device 120/130 (via, for example, a light source unit 120) so as to be capable of delivering the distending media to the endoscopic device 120/130 according to one embodiment of the present invention. According to some embodiments, the insufflating system 100 comprises a controller 101 for detecting a pressure level within a lumen of the endoscopic device 120/130 (such as, for example, the lumen 124 of the endoscope 130 and/or a lumen defined in the tubing set 106 in fluid communication between the insufflating system 100 and the light source unit 120). The insufflating system 100 embodiments of the present invention may also comprise a valve assembly 103 in communication with the controller 101. The valve assembly 103 may also be in fluid communication between the source 110 of distending media and the components of the endoscopic device 120/130 for delivering the distending media to the endoscope 130 and adjusting a flow rate of the distending media delivered to the endoscope 130 (via the light source unit 120, for example) in response to the detected pressure level so as to prevent excess supply and waste of the distending media. As shown in FIG. 1, the insufflating system 100 of the present invention may be operably engaged with a conventional light source 120 and/or endoscope 130.

Some embodiments of the present invention may comprise an insufflating system 100 consisting of an electro-pneumatic insufflator connected to a gastrointestinal endoscope 130, via a conventional endoscope light source unit 120, as shown generally in FIG. 1). Connection between the insufflating system 100 and the light source unit 120 may be accomplished via a tubing set 106 disposed between an outlet 208 of the insufflating system 100 and a connection in the water bottle 121 of the light source unit 120. According to various embodiments of the present invention, the tubing set 106 may comprise disposable medical-grade and/or biocompatible tubing that may be replaced and/or discarded after each use. Thus, the insufflating system 100 of the present invention may be isolated from pathogens that may be introduced into the endoscope 130 and/or light source unit 120 during the course of an endoscopic procedure. Furthermore, some embodiments of the insufflating system 100 of the present invention may further comprise a filter device 107 in fluid communication between an output of the valve assembly 103 of the insufflating system 100 and a lumen 124 of the endoscopic device 130. Furthermore, as shown in FIG. 1, in some embodiments, the filter device 107 may be in operably engaged in fluid communication between an output of the valve assembly 103 of the insufflating system 100 and an input to the light source unit 120 (such as, for example, a port defined in the water bottle 121 of the light source unit 120) so as to prevent passage of a pathogen from the endoscopic device 130 to the valve assembly 103 of the insufflating system 100 of the present invention. For example, should a clinician change the water bottle 121 and inadvertently spill liquid back through the tubing set 106, the filter device 107 may prevent the passage of a pathogen to the valve assembly 103. According to various system embodiments of the present invention, the filter device 107 may include, but is not limited to: a biological filter, a hydrophobic filter, and combinations thereof.

In a manner similar to conventional endoscope practice, the attachment of the insufflating system 100 of the present invention (as shown generally in FIG. 1) may provide a flow of insufflating media and/or irrigation water to at least one of the lumens 124 of the endoscope 130. However, the system embodiments of the present invention may also provide an "on-demand" flow of distending and/or insufflating media from a source 110 of distending media to the endoscope 130 in response to a user control input via the control portion 135 of the endoscope.

As one skilled in the art will appreciate, conventional gastrointestinal endoscopes may require a nominal flow rate within the range of 3 Liters per minute to a maximum delivery pressure of 350 to 400 mm Hg in order to properly insufflate and/or irrigate an anatomical cavity defined in a subject. These exemplary performance specifications are independent of insufflating media ($CO_2$ or room air, for example), and method of delivery (an air pump integrated with the light source unit 120, or electro-pneumatic distending media regulation as provided by the various embodiments of the present invention). One particular advantage of the various embodiments of the insufflating system 100 of the present invention is the "on demand" provision of distending media at an insufflating flow rate (i.e. at about 3 liters per minute) when an endoscope operator manipulates the control section 135 of the endoscope to send distending media through the insufflating flow pathway 150 at the distal end of the endoscope 130. In addition, the insulating system 100 embodiments of the present invention further provide for a conservative sensing flow rate (0.5 liter/minute, for example) to be expelled to atmosphere via a sensing flow pathway 140, at the endoscope control section 135 while the operator of the endoscope 130 does not require the full insufflating flow rate. Thus, distending media (such as bottled carbon dioxide) may be better conserved. Furthermore, embodiments of the present invention may prevent the venting of large amounts of carbon dioxide into the ambient clinical environment (such as the endoscopy suite within a medical practice or hospital). Conventional systems and methods for supplying distention media from a light source air pump or via a mechanical $CO_2$ regulating apparatus connected to the endoscope 130 do not provide for such an "on-demand" provision of distending media that may be responsive to the control inputs of the clinician or other endoscope operator.

According to various embodiments of the present invention, the controller 101 of the insufflating system 100 may be capable of detecting a pressure level within the lumen 124 of the endoscope 130. The detectable pressure differential between the need for an insufflating flow rate (corresponding to the conduction of distending media through the insufflating flow pathway 150) and a sensing flow rate (corresponding to the conduction of distending media through the sensing flow pathway 140) may be inherent to the particular endoscope 130 utilized in a given procedure. When the air-water valve of the control section 135 is open, there exists a relatively low constant pressure level within the endoscope lumen 124. Furthermore, when the air-water valve is closed, pressure within the endoscope lumen 124 increases as a result of the flow resistance associated with the additional length of the endoscope lumen (leading from the control section 135 to the insufflating flow pathway 150) and the pressure level of the anatomical cavity under examination. For example, as distending media (such as an insufflating gas) flows through the endoscope with the air-water valve open, lumen pressure upstream of the endoscope control section 135 may be on the order of 10 to 30 mm Hg. When the air-water valve is closed, the additional flow resistance imparted by the additional length of endoscope flow lumen downstream of the endoscope control may increase the detectable pressure level in the endoscope lumen 124 and/or at an insufflating media connection (for example, at the water bottle 121 port) to approximately 50 to 150 mm Hg with a relatively constant flow rate. Similarly when the air-water valve is re-opened, upstream pressure at the insufflating media connection (for example, at the water bottle 121 port) may return to the lower pressure.

Thus, according to various insufflating system 100 embodiments of the present invention, the controller 101 may comprise a pressure transducer for detecting a pressure within a lumen of the endoscopic device. Some embodiments of the insufflating system 100 may comprise an in-line outlet pressure transducer (as part of the controller 101) that may measure pressure levels at the endoscope 130 media connection upstream of the control section 135. In some embodiments, the controller 101 may be capable of detecting a pressure within a lumen 124 of the endoscope 130. In other embodiments, the controller 101 may be capable of detecting a pressure within a lumen defined in the tubing set 106 in fluid communication with a port defined in the water bottle 121 of a conventional light source unit 120 that may be provided as part of a conventional endoscopic device. In yet another embodiment, the controller 101 may be capable of detecting pressure with an internal lumen internal to the light source unit 120 upstream of the endoscope 130 connection to the light source unit 120. The outlet pressure transducer may thus be capable of resolving the pressure differential shown generally in FIGS. 3-5 as an operator periodically closes and opens the air-water valve located on the endoscope control section 135 during a procedure. During the course of the procedure the controller 101 portions of the insufflating system 100 may monitor the output of the pressure transducer. In some system embodiments of the present invention, the controller 101 may further comprise a memory device 108 in communication therewith for storing, for example, a pressure threshold (see elements 305, 401, 402 of FIGS. 3-5). The memory device 108 and/or controller 101 may further comprise programmed logic (see FIGS. 6-9, for example) to make the decision to control the valve assembly 103 to output a (relatively low) sensing flow rate when the air-water valve is open (and emitting distending media via the sensing flow pathway 140) or control the valve assembly 103 to output a (relatively high) insufflating flow rate when the air-water valve is closed (and emitting distending media via the insufflating flow pathway 140 at a distal end of the endoscope 130). According to some insufflating system 100 embodiments, the valve assembly 103 may comprise an electro-pneumatic valve assembly or other electromechanical mechanism for controlling the flow rate of a distending media that may be delivered from a bottled source 110 (such as a bottle of compressed carbon dioxide) via the insufflating system 100 in response to the pressure levels detected by the controller 101 (and/or a pressure transducer that may be provided therein). According to the various embodiments of the present invention, the insufflating flow rate may be between about 1 and 20 liters per minute and the sensing flow rate may be between about 0.05 and 0.5 liters per minute.

As shown generally in FIG. 1, various embodiments of the insufflating system 100 may be in fluid communication between an endoscopic device (including, for example, a light source unit 120 and an endoscope 130) and a source 110 of distending media, such as a bottle of compressed insufflating media. According to various embodiments of the present invention, the distending media may include, but is not limited to: carbon dioxide; anti-spasmodic gaseous media; relaxant gaseous media; and combinations of such media that may serve as distending media in an endoscopic procedure. While embodiments of the present invention are particularly useful for conserving bottles distending media (such as carbon dioxide) and for preventing the excess venting of carbon dioxide into the endoscopy suite, the insufflating system 100 embodiments of the present invention may also be used to deliver distending media from a variety of sources 110, including for example, bottles of compressed air (including nitrogen components).

Figure 2:
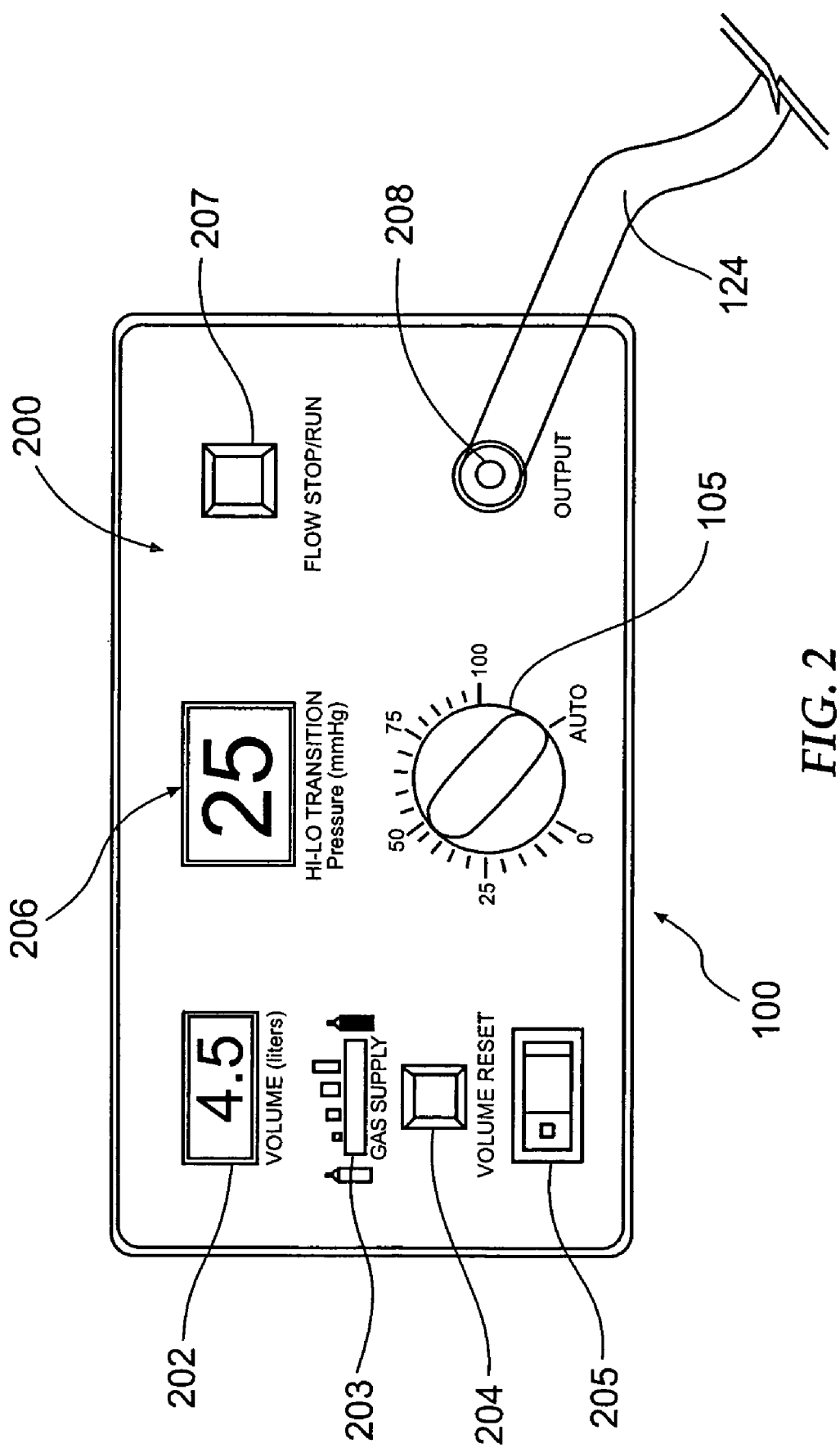
FIG. 2 shows a non-limiting schematic of a front panel user interface of an insufflating system according to one embodiment of the present invention.

Some embodiments of the insufflating system 100 of the present invention may further comprise a user interface 200 (see FIG. 2) for receiving a user input (such as a pressure threshold (see element 305, FIG. 3, for example) such that the insufflating system 100 may adequately respond to the detected changes in pressure within the components 120/130 of the endoscopic device. As shown in FIG. 2, the user interface 200 may comprise a front panel of the insufflating device 100. The user interface 200 may comprise a variety of informational displays to display insufflating system 100 status (and/or the status of the distending media supply 110 or components 120/130 of the endoscopic device). For example, the user interface 100 may comprise a volume display 202 for indicating a volume of distending media delivered to the endoscopic device 120/130. The user interface may also comprise a remaining volume display 203 for indicating a volume of distending media remaining in the distending media source 110. The user interface 200 may also comprise a user input display 206 for indicating a pressure threshold and/or a high pressure transition point (as discussed in further detail below) that may be input by an operator via a control dial 105 that may also be provided as a component of the user interface 200. Furthermore, the user interface may also comprise buttons and/or switches for receiving a variety of user inputs. For example, a "volume reset" button 204 may be provided to reset the volume displays 202, as described above (for example, when a new procedure is initiated). The user interface 200 may also comprise, for example, a "run/stop" control button 207 for selectively beginning and/or ceasing the flow of distending media via the insufflating system 100. In addition the insufflating system 100 user interface 200 may also comprise a power button 205 (such as a rocker switch) for shutting off electrical power to the controller 101, valve assembly 103 and/or other components of the insufflating system 100 when the system is not in use. Finally, according to some embodiments of the insufflating system 100, the user interface 200 may also comprise a flow output 124 for establishing fluid communication between the insufflating system 100 and the components 120/130 of the endoscopic device (via, for example, a tubing set 106 and/or a filter device 107, as described above).

The user interface 200 and/or controller 101 of the insufflating system 100 may, in some embodiments, provide additional functional features. For example, if the transition pressure (see element 305, FIG. 3, and the transition display 206, FIG. 2) on the control dial 105 is set to 0 (zero), flow rate transitioning may be disabled and the insufflating system 100 may only deliver distending media at insufflating (high) flow rate for those clinicians preferring for the insufflating system 100 to not transition automatically. Furthermore, the system 100 may also automatically pause the delivery of distending media at 25 liter increments. For normal endoscopy procedures, the typical distention media volume should be less than this volume threshold. Thus if an operator either forgets to stop the device (via the control input 207) at the end of a procedure or suspends the procedure for whatever reason without shutting down the insufflating system 100, the system 100 will automatically pause when the volume reaches 25 liters to prevent unintended waste of distending media. Should additional media be required, the operator simply presses the start button 207 to resume operating and the volume display will increment up from 25 liters until it pauses again at 50 liters. The operator is able to reset the volume (via the volume reset button 204) as they see fit either between procedures or during procedures.

Figure 3:
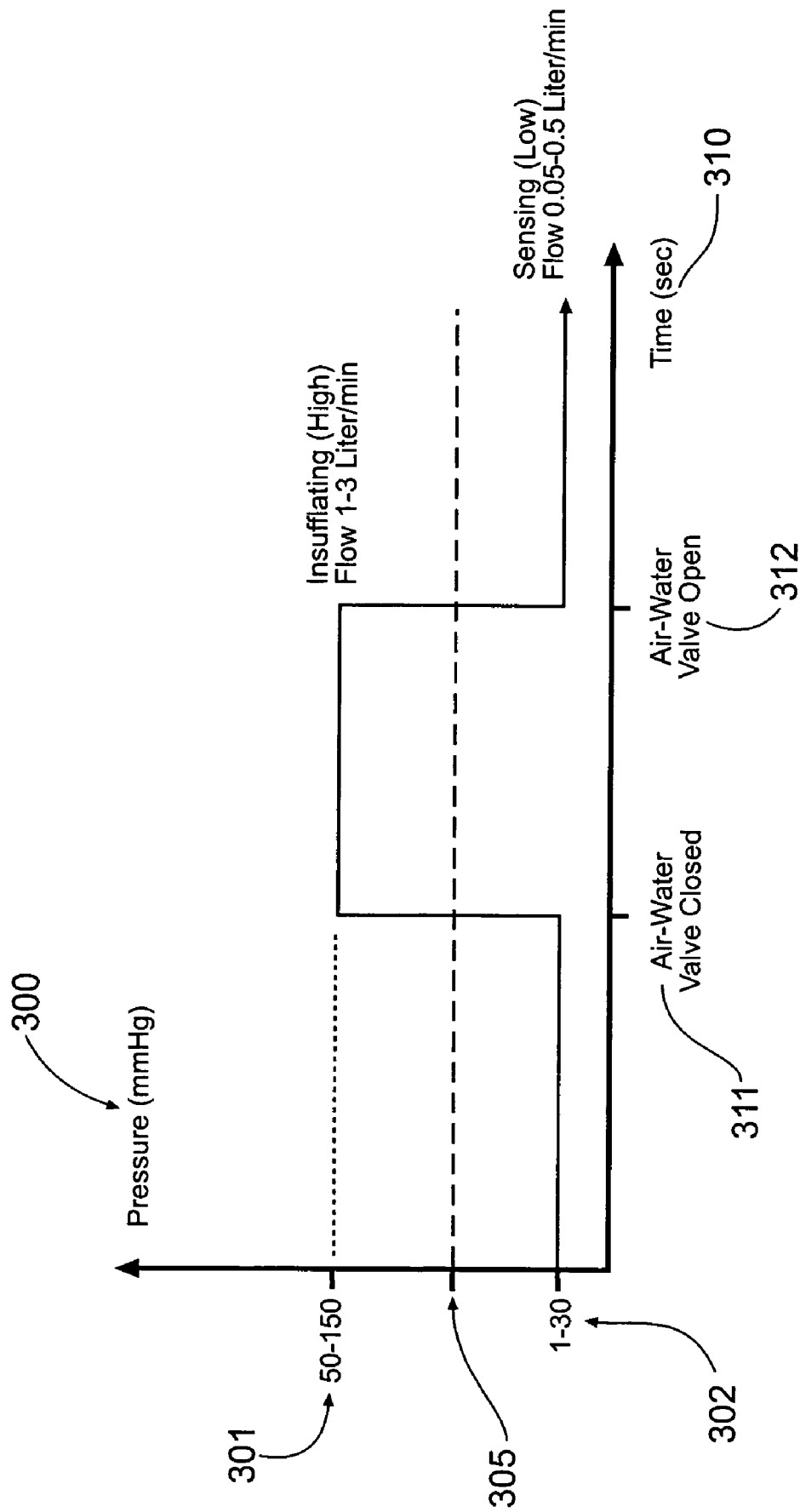
FIG. 3 shows a non-limiting time versus pressure plot showing a plot of detected pressure in a lumen of an endoscopic device versus time during an exemplary portion of an insufflating procedure in relation to a single defined pressure threshold.

According to some embodiments of the present invention, the user interface 200 may be capable of receiving (via the control dial 105, for example) a user input comprising at least one pressure threshold (see FIG. 3, element 305). In some embodiments, the system 100 may further comprise a memory device 108 for storing the pressure threshold 305 such that the controller 101 may control the valve assembly 103 to adjust the flow rate to an insufflating flow rate if the detected pressure is greater than the pressure threshold 305. Furthermore, the controller 101 may control the valve assembly 103 to adjust the flow rate to a sensing flow rate if the detected pressure is less than the at least one pressure threshold 305. For example, referring to FIG. 3, which shows simplified plot of detected pressure 300 versus time 310 for an exemplary endoscope procedure, the low detected pressure 302 during sensing flow may be about 20 mm Hg and the insufflating flow (high) detected pressure 301 may be about 60 mm Hg. A threshold pressure 305 (as input by an operator via a control dial 105) may be established midway between these detected pressures 301, 302 (40 mm Hg, for example). Thus, as an operator closes the air-water valve 311 at the control portion 135, the lumen pressure detected by the controller 101 increases. When the controller 101 ascertains that the threshold 305 (40 mm Hg) lumen pressure has been detected, the controller 101 may then control the valve assembly 103 to increase the distending media flow rate from the low sensing flow rate to the high insufflating flow rate. As flow continues at the higher flow rate, a "high" equilibrium pressure 301 of 60 mm Hg may be detected in the endoscope lumen. The system 100 may then continue to supply distending media to the endoscopic device 120/130 at the high distending flow rate for the duration of the air-water valve closure. Finally, as an operator opens the air-water valve 312 after the insufflating flow rate has been established, pressure in the endoscope lumen decreases. Should the pressure drop cause the pressure, as measured by the insufflating system 100, to fall below the 40 mm Hg pressure threshold 305, the controller 101 may detect an open air-water valve and automatically set the flow parameters to back to a sensing low flow, thereby curtailing the amount of gas being discharged to the surrounding clinical atmosphere when the endoscope control section 135 is idle.

Figure 4:
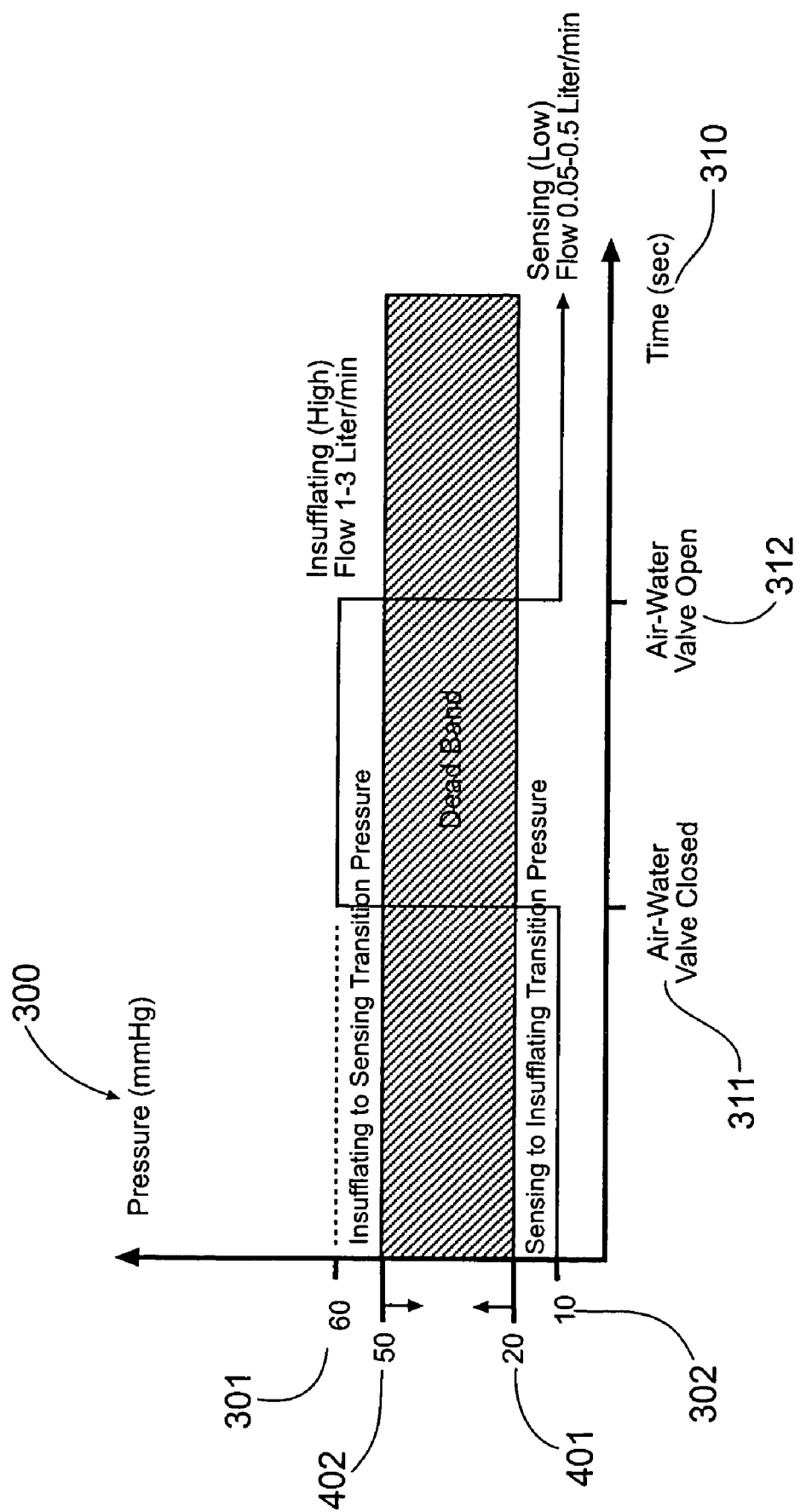
FIG. 4 shows a non-limiting time versus pressure plot showing a plot of detected pressure in a lumen of an endoscopic device versus time during an exemplary portion of an insufflating procedure in relation to a low pressure transition point and a high pressure transition point.

Referring generally to FIG. 4, according to some system embodiments, the user interface 200 may be capable of receiving (via the control dial 105, for example) a user input comprising a low pressure transition point 401 and a high pressure transition point 402. Furthermore, according to some embodiments, the system 100 may be pre-programmed with a low pressure transition point 401 (which may be stored, for example in a memory device 108 in communication with the controller 101) such that the control dial 105 may be used to input the high pressure transition point 402 which defines the transition between low sensing flow and high insufflating flow so as to simplify the pressure inputs that an operator must enter to effectively operate the insufflating system 100. According to some such embodiments, the controller 101 may control the valve assembly 103 to adjust the flow rate from a sensing flow rate to an insufflating flow rate if the detected pressure 300 rises above the low pressure transition point 401. Furthermore, the controller 101 may be further adapted to control the valve assembly 103 to adjust the flow rate from the insufflating flow rate to the sensing flow rate if the detected pressure 300 falls below the high pressure transition point 402. For example, as shown in the pressure 300 versus time 310 plot of FIG. 4, some insufflating system 100 embodiments of the present invention may allow for an operator to specify two pressure transition set points 401, 402. The use of high and low pressure transitions 401, 402 may allow the insufflating system 100 to be effectively used with a wider range of endoscopic devices 120/130. For example, a single transition point 305 (as shown in FIG. 3) may be effective only in cases where opening the air-water valve of the control portion 135 produces a sufficient pressure drop in the lumen to result in a detected pressure that is less than the threshold pressure 305. System embodiments allowing for two pressure transition points (401, 402), one for sensing to insufflating flow (401) and the other (402) from insufflating to sensing flow may improve system 100 performance and response characteristics by eliminating the pneumatic latency associated with a single transition set point 305. By way of non-limiting example, the pressure time history shown in FIG. 4 may be bounded by two transition pressures 401, 402 to define a "dead band." As shown generally in FIG. 4, a low pressure transition point 401 (20 mm Hg, for example) is provided above the 10 mm Hg equilibrium pressure 302 associated with sensing flow 140 (see FIG. 1) with the air-water valve open and a high pressure transition point 402 (50 mm Hg, for example) is provided just below the 60 mm Hg equilibrium pressure for insufflating flow 150 (see FIG. 1) with the air-water valve closed.

Figure 5:
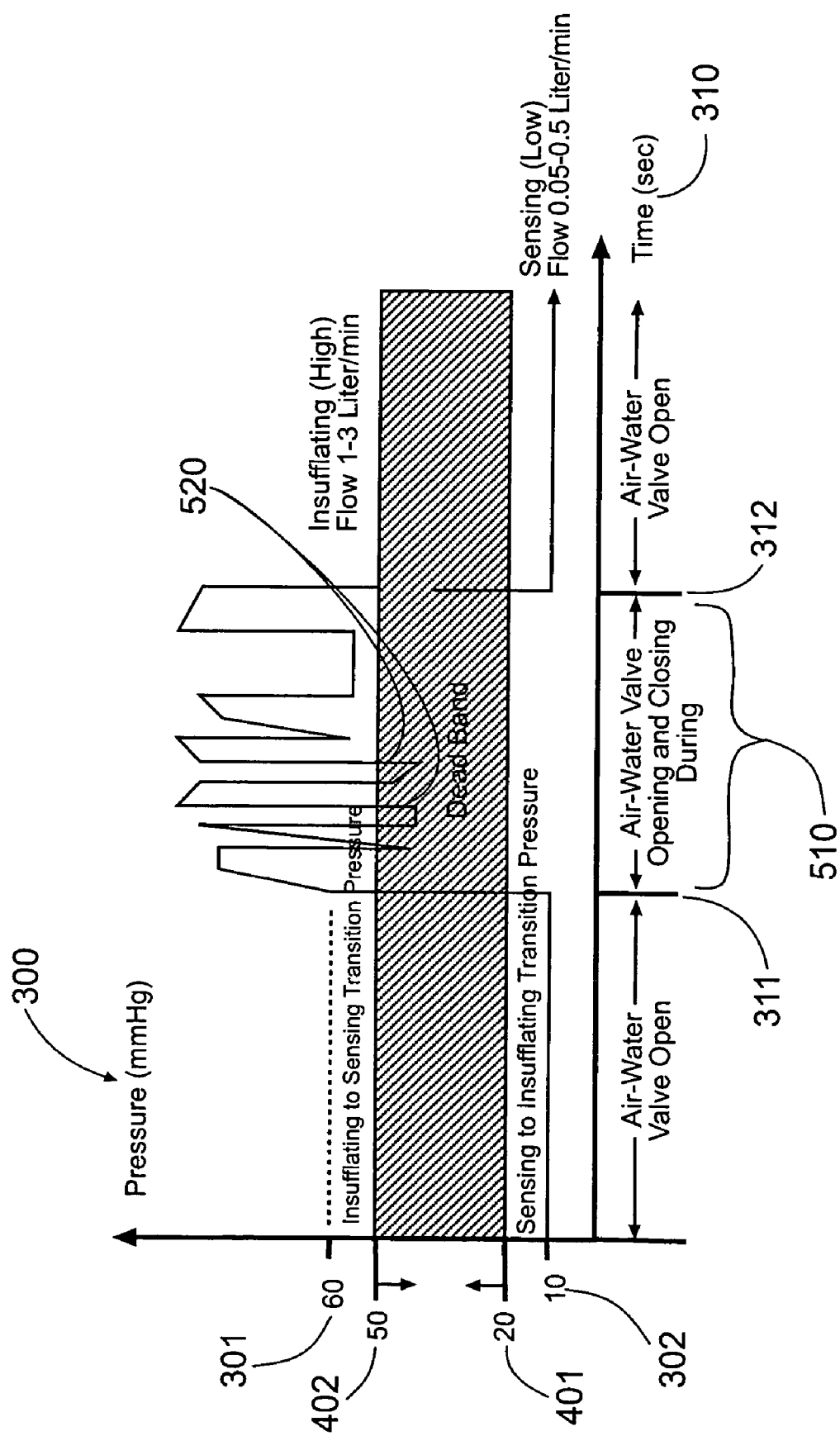
FIG. 5 shows a non-limiting time versus pressure plot showing a plot of detected pressure in a lumen of an endoscopic device versus time during an exemplary portion of an insufflating procedure in relation to a low pressure transition point, high pressure transition point, and a defined time limit.

According to some other system embodiments of the present invention, the controller 101 (or a memory device 108 provided therein and/or in communication therewith) may comprise a programmed time limit 510 (see FIG. 5, for example). The time limit 510 may thus provide a timed "filter" for imposing the low and high pressure transition points 401, 402 as shown generally in FIG. 5. In other embodiments, the user interface 200 may be capable of receiving a user input comprising such a time limit. Thus, according to some system 100 embodiments, the controller 101 may control the valve assembly to adjust the flow rate from a sensing flow rate to an insufflating flow rate if the detected pressure 300 rises above the low pressure transition point 401 for a time period exceeding the time threshold 510. Furthermore, the controller 101 may control the valve assembly 103 to adjust the flow rate from the insufflating flow rate to the sensing flow rate when the detected pressure 300 falls below the high pressure transition point 402 for a time period exceeding the time limit 510. For example, as shown in the exemplary pressure 300 versus time 310 plot of FIG. 5, two pressure transition points 401, 402 may be used in conjunction with filtering algorithms (defined, for example, by pre-programmed time thresholds 510) to minimize erroneous or unintended changes between sensing and insufflating flow. The necessity of such filtering results from the clinical reality that the high insufflating flow rate rarely exhibits equilibrium pressures 301 for long periods because an operator of the endoscope 130 may repeatedly opens and closes the water valve of the control portion 135 quickly during endoscopic examination. It will be appreciated by one skilled in the art that such changes may be experimentally observed by measuring pressure time histories of the endoscope gas lumen upstream of the control section 135 during active navigation. For example, FIG. 5 shows an exemplary pressure 300 versus time 310 history that may be indicative of an actual clinical endoscopic procedure.

As shown generally in FIG. 5, once active endoscopic navigation begins and the flow transition from sensing to insufflating flow has taken place, endoscope pressure 300 as measured by the insufflating system 100 of the present invention may vary up and down periodically in synchrony with modulation of the air-water flow valve of the control section 135 of the endoscope 130. The amplitude of such spikes may produce transient dips 520 below the high pressure transition point 402. To avoid inadvertent and clinically disruptive transitions to the low sensing flow, the controller 101 of the present invention (having the benefit of a pre-programmed time limit 510 and/or a timer device (not shown)) may scrutinize the detected pressure 301 for a pre-determined period of time 510. Only if all such detected pressures 300 within this time window 510 are below the high pressure transition point 402, will the insufflating system 100 (or a controller 101 included therein) automatically control the valve assembly 103 to reduce the flow to the sensing flow rate. The duration of the time threshold 510 may be based upon clinical experience to date and, thus may be defined, in some embodiments to be in the range of 2 to 5 seconds. Thus, should the pressure 300 detected by the controller 101 of the insufflating system 100 remain continuously below the high pressure transition point 402 for the programmed time limit 510, it may be indicative of a deliberately open air-water valve and as such it is desirable to switch to the lower gas saving sensing flow rate until the air-water valve is closed again.

According to other embodiments of the system 100 of the present invention, the controller 101 collect and store pressure 300 versus time 310 plots (shown, for example in FIGS. 3-5) so as to adaptively "learn" to automatically apply high and low pressure thresholds 402, 401 and time limits 510 so as to more effectively respond to detected changes in pressure within a lumen of the endoscopic device. The user interface 200 (see FIG. 2) may include a control dial 105 such that an operator may select an "auto" mode for initiating such an "adaptive" control routine. In some embodiments, the insufflating system 100 may automatically determine the high pressure transition point 402. As described above, detected pressure 300 upstream of the endoscope control section 135 may oscillate during active endoscope usage or navigation. Observed pressure oscillations are of such frequency that the 2-5 second time limit 510 of the previously-discussed embodiments may be adequate in almost all cases where the open air-water valve pressure falls below the high pressure transition point 402. However, in some particular clinical circumstances (perhaps exhibited with the use of certain endoscopic devices) the opening of the air-water valve at the control portion 135 may not result in detected pressure 300 that falls below the high-pressure transition point 402. Thus, in some instances, the previously-discussed embodiment may not produce the intended insufflating to sensing flow transition. Thus, according to some system 100 embodiments of the present invention, added logic could be programmed into a memory device 108 and/or hardwired into a controller 101 of the insufflating system 100 (see FIG. 9, for example) such that the high and/or low pressure transition points 401, 402 may be adaptively determined real time by a suitable stability criterion of the detected pressure 300.

For example, rather than having the programmed logic of the controller 101 look for a series of pressure 300 measurements representative of a pre-determined period of time 510 to all be below a pre-programmed pressure threshold 402 before transitioning, the adaptive system could first look for a continuous series of pressure measurements 300 of nearly identical magnitude stored in memory 108. Such a stability condition may occur, for example, when the air-water valve of the control portion 135 is left open after active endoscopic navigation by an operator has stopped. If the series of pressure measurements 300 remain stable (within a pre-defined tolerance band) for a predefined number of samples followed by a pre-determined period of time 510, the insufflating system 100 may transition from insufflating to sensing flow without the need for any reference to any pre-set or pre-programmed transition pressure 402. The logic steps of an associated method for adaptive learning are shown generally in FIG. 9.

Thus, in some insufflating system 100 embodiments, the memory device 108 may include a "Pressure Stability Checking Memory" which may comprise a finite array variable with supporting code that may either stack or provide a reference pointer to stored data providing a sliding time window or epoch. Such a time window or epoch would move in synchrony real time with an endoscopic procedure such that an appropriate retrospective pressure history may be available for evaluation. Within such a grouping of pressure history data being processed in real-time during the procedure, a number of different types of algorithms and supporting logic could be applied to identify pressure stability that may be indicative of an open air-water valve (and the need for a lower, distending media-saving, sensing flow rate).

A similar stability approach and associated logic could be applied to that shown generally in FIG. 9 to handle the transition from sensing (low) flow rates to insufflating (high) flow rates thereby making the insufflating system 100 automatically adaptive to most, if not all, endoscope 130 and/or light source unit 120 types and brands. In yet another embodiment of the "adaptive" approach, artificial intelligence techniques may also be applied to augment such an adaptive system. More particularly, ancillary device memory 108 and processing algorithms may further scrutinize pressure time histories indicative of certain usage patterns that may be practice or user specific. In this case, such collective histories can be used to develop user/clinical specific anticipatory response logic to further optimize the performance of the device for a specific endoscope operator or clinical application (such as a specific procedure type).

FIGS. 6-9 generally show several alternative method embodiments of the present invention for delivering distending media (from a source 110 of distending media, for example) to an endoscopic device (including a light source unit 120 and/or endoscope 130) in fluid communication with the source 110 of distending media. As described further below, the various method embodiments may be performed as the steps of a computer program product that may be executed by an electronic controller 101 (in communication with a memory device 108 and a valve assembly 103) that may be included as part of an electro-pneumatic insufflating system 100 that may be in fluid communication between the distending media source 110 and the components 120/130 of an endoscopic device.

Figure 6:
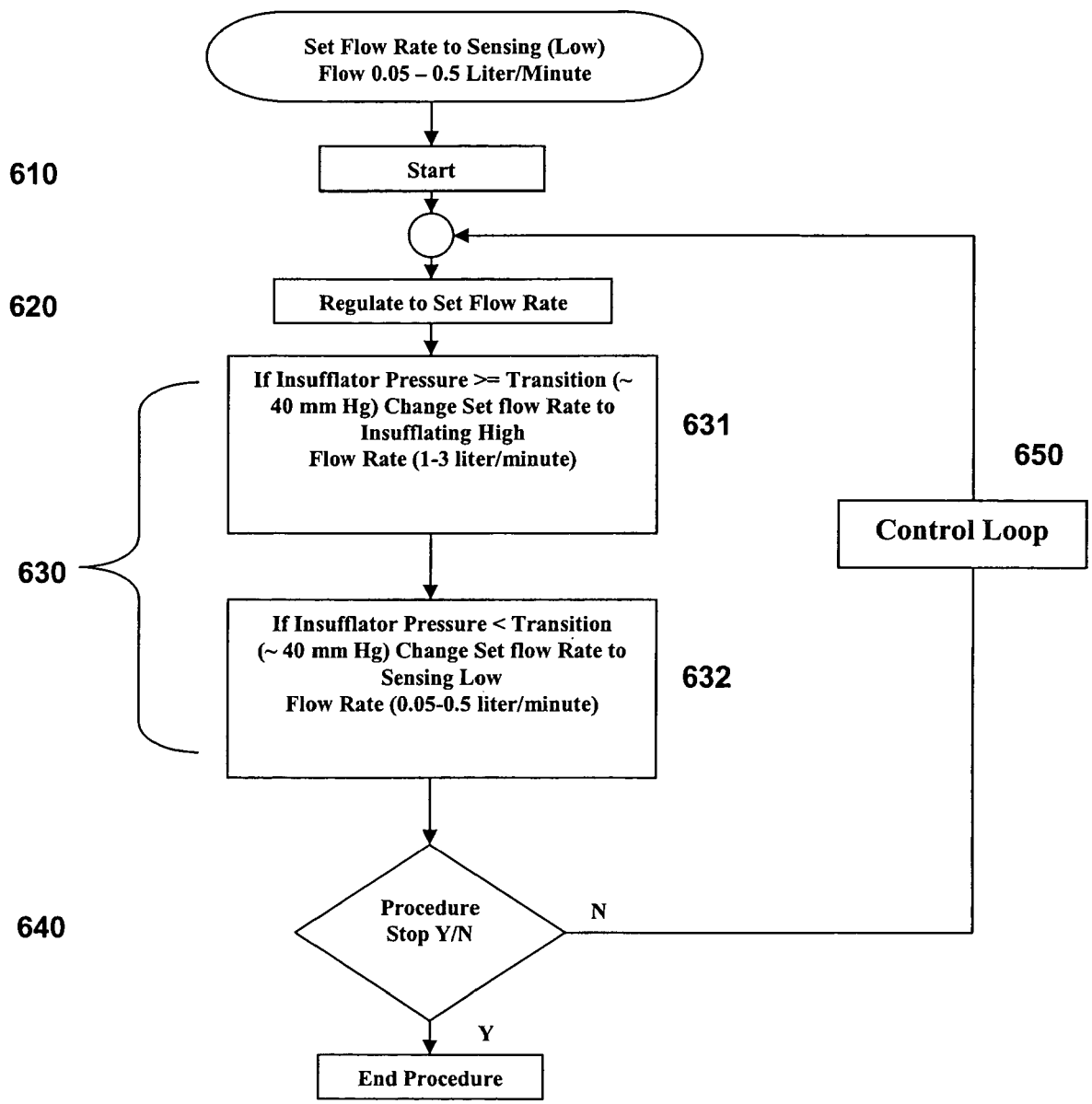
FIG. 6 shows a non-limiting flow diagram of a method and/or computer program embodiment of the present invention including pressure detecting, delivery, and flow rate adjusting steps, wherein the adjusting step comprises adjusting a flow rate in response to the relative value of a detected pressure with respect to a threshold pressure.
Figure 7:
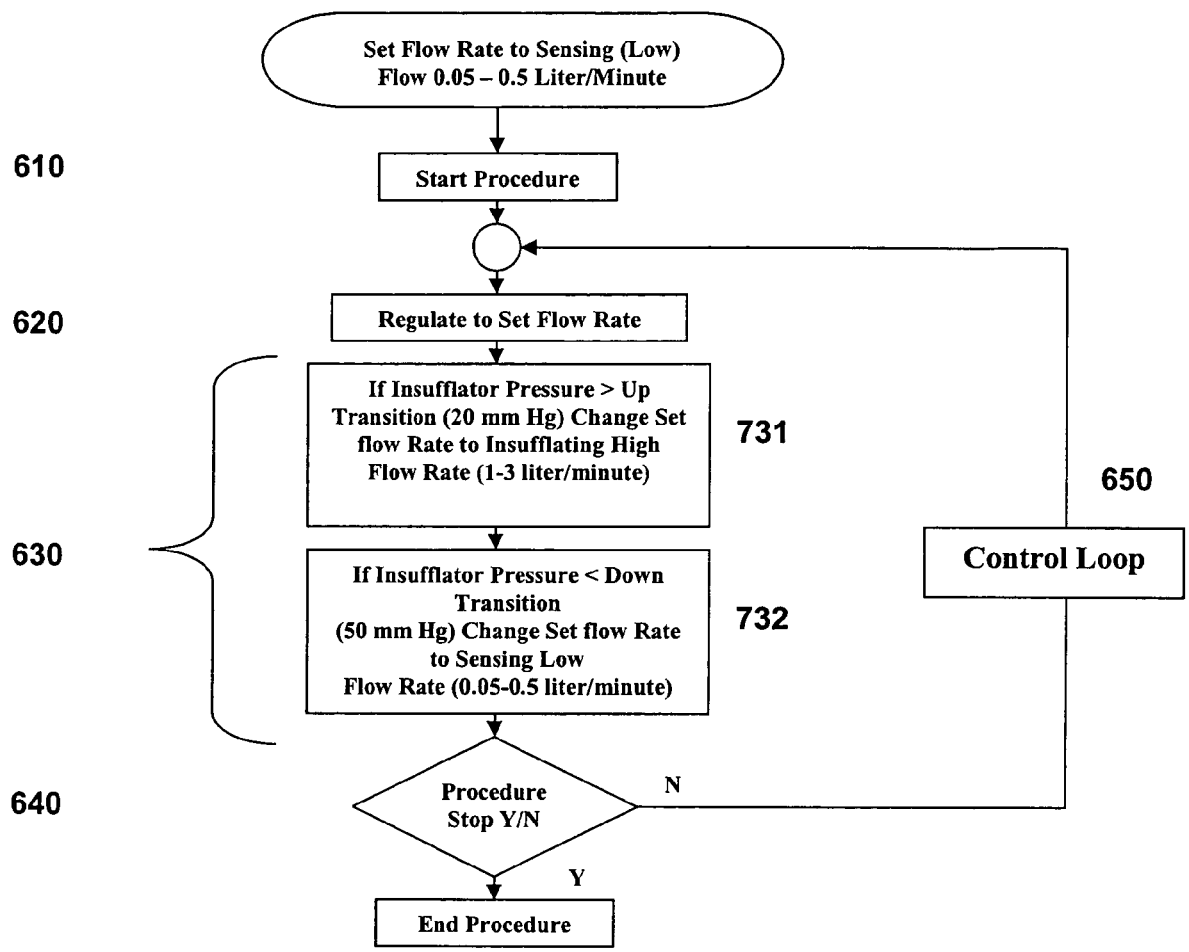
FIG. 7 shows a non-limiting flow diagram of a method and/or computer program embodiment of the present invention including pressure detecting, delivery, and flow rate adjusting steps, wherein the adjusting step comprises adjusting a flow rate in response to the relative value of a detected pressure with respect to both a low pressure transition point and a high pressure transition point.

According to one method embodiment of the present invention, shown in FIG. 6 for example, the method may comprise steps including: step 610 for detecting a pressure level (and/or conditionally adjusting a flow rate in response to the detected pressure) within a lumen 124 (and/or a lumen defined by a tube set 106 interposed between the insufflating system 100 and the light source unit 120) of the endoscopic device; a delivering and/or regulating step 620 for regulating the delivery of the distending media to the endoscopic device; and a detecting and/or conditionally adjusting step 630 for adjusting a flow rate of the distending media delivered to the endoscopic device in response to the detected pressure level so as to prevent excess supply and waste of the distending media. Step 610 (as shown generally in FIGS. 6-9 may comprise detecting a pressure and/or conditionally adjusting a flow rate of distending media in response to the detected pressure. Furthermore, as described generally above, the detecting and/or conditionally adjusting step 630 may comprise adjusting a flow rate of the distending media to a (low) sensing flow rate (between about 0.05 and 0.5 liters per minute) if the detected pressure is indicative of an open air/water valve at the control section 135 of the endoscope that results in the venting of distending media through a sensing flow pathway 140 at the control section 135. Furthermore, the detecting and/or conditionally adjusting step 630 may comprise adjusting a flow rate of the distending media to a higher, insufflating flow rate (between about 1 and 20 liters per minute) if the detected pressure is indicative of an closed air/water valve at the control section 135 of the endoscope that results in the direction of distending media through an insufflating flow pathway 150 and into a subject anatomical cavity via a distal end of the endoscope 130.

As shown in FIGS. 6-9, the method may also comprise step 640 for detecting a "procedure stop" command that may be initiated by an operator pressing the "flow stop/run" button 207 that may be included as part of the user interface 200 according to some system 100 embodiments of the present invention. Furthermore, the methods may also comprise a control feedback loop 650 for regulating the flow rate of distending media in response to the detected pressures (as described in further detail below).

According to some method embodiments of the present invention, the method may further comprise filtering a fluid pathway (such as a disposable tubing set 106) in fluid communication between the source 110 and the endoscopic device (see elements 120 and 130 of FIG. 1) so as to prevent passage of a pathogen from the endoscopic device to the source of the distending media. The filtering step may comprise, for example, providing a filter device 107 in fluid communication between the insufflating system 100 of the present invention and the light source unit 120 of the endoscopic device. According to various embodiments, the filter device 107 may comprise, for example, a biological filter, a hydrophobic filter, or another filter device capable of preventing the passage of a pathogen from the endoscopic device to the valve assembly 103 of the insufflating system 100.

Furthermore, some method embodiments may further comprise receiving a user input for controlling the detecting and/or conditionally adjusting step 630. For example, the receiving step may comprise providing a control dial 105 as part of a user interface 200 (see FIG. 2, for example) that may be provided as part of the insufflating system 100 of the present invention. Thus, an operator may input one or more pressure thresholds 305 (see FIG. 3, for example) and or one or more low and high pressure transition points 401, 402 (see FIG. 4, for example) that may be stored in a memory device 108 such that the controller 101 of the system 100 embodiments of the present invention may compare one or more of the user inputs to a detected pressure (obtained in near-real time, for example in step 610) in order to perform the detecting and/or conditionally adjusting step 630.

As described above with respect to the system 100 embodiments of the present invention, the user input (received by a user interface 200, for example, via a control dial 105, see FIG. 2) may comprise at least one pressure threshold (see element 305, FIG. 3). Thus, the detecting and/or conditionally adjusting step 630 may further comprise step 631 for adjusting the flow rate to an insufflating flow rate if the detected pressure is greater than the at least one pressure threshold 305. Furthermore, the detecting and/or conditionally adjusting step 630 may also comprise step 632 for adjusting the flow rate to a sensing flow rate if the detected pressure is less than the at least one pressure threshold 305. Thus, according to one exemplary method embodiment, shown in the flow diagram of FIG. 6, the method may first comprise a startup phase wherein a flow rate is set to a sensing flow rate (low) corresponding to the venting of distending media from the sensing flow pathway 140 (see FIG. 1). The method may then comprise step 610 (start procedure, for example) that may include detecting the pressure within a lumen of the endoscopic device. Step 620 comprises regulating the delivery of the distending media to the endoscope at a set flow rate (sensing flow rate, to begin the procedure). Then step 630 comprises comparing the detected pressure levels to one or more pressure thresholds in order and adjusting the flow rate accordingly. Thus, electronic embodiments of the method (as shown schematically in FIG. 6) may include a feedback loop 650 for adjusting the flow rate of the delivered distending media in response to the pressure comparisons that may occur as part of the detecting and/or conditionally adjusting step 630.

In other method embodiments, the user input may comprise a pair of pressure transition points (high 402 and low 401, as shown in FIG. 4, for example). According to some embodiments, the user input may comprise only the high 402 pressure transition point while the controller 101 provided as part of some system 100 embodiments may be pre-programmed with a low pressure transition point 401. In one such exemplary method embodiment, shown schematically in FIG. 7, the detecting and/or conditionally adjusting step 630 may further comprise component steps 731 and 732 for comparing the detected pressure level in the endoscope lumen to the high 402 and low 401 pressure transition points. For example, step 731 may comprise adjusting the flow rate from a sensing flow rate to an insufflating flow rate if the detected pressure rises above the low pressure transition point 401 (which may be indicative of the closure of the valve included in the control portion 135 and the direction of distending media towards the insufflating flow pathway 150 (shown in FIG. 1)). Furthermore, step 732 may comprise adjusting the flow rate from the insufflating flow rate to the sensing flow rate if the detected pressure falls below the high pressure transition point 402 (which may be indicative of the opening of the valve included in the control portion 135 and the venting of distending media through the sensing flow pathway 150 (shown in FIG. 1)).

Figure 8:
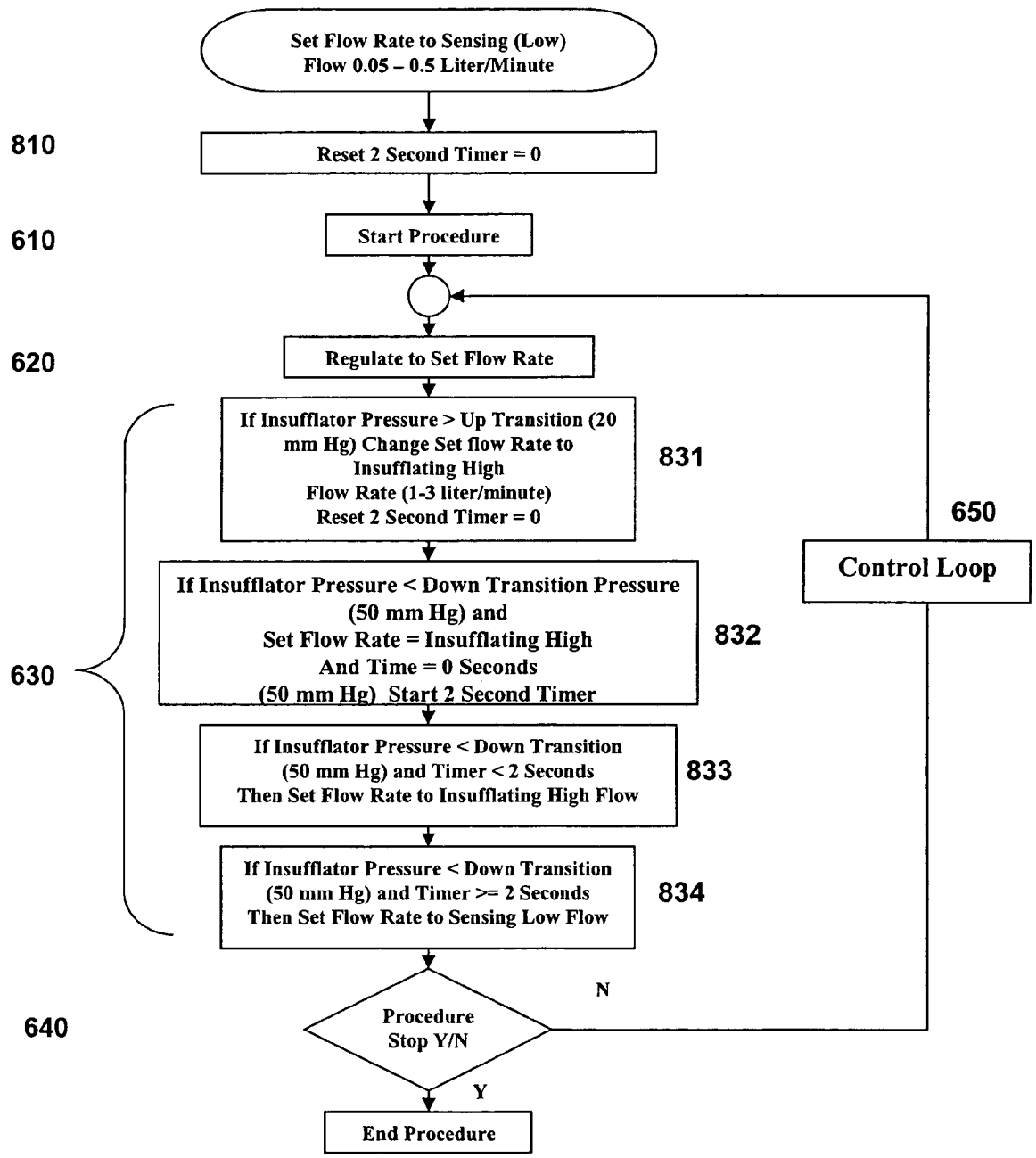
FIG. 8 shows a non-limiting flow diagram of a method and/or computer program embodiment of the present invention including pressure detecting, delivery, and flow rate adjusting steps, wherein the adjusting step comprises adjusting a flow rate in response to the relative value of a detected pressure with respect to: a low pressure transition point; a high pressure transition point; and a time limit.

As described above, some system 100 embodiments of the present invention may provide a programmed time limit 510 (see FIG. 5) for filtering and/or disregarding momentary changes in detected pressure 300 that may cross one or more of the low 401 and high 402 pressure transition points such that the system 100 may be less likely to inappropriately shift from the delivery distending media at high insufflating flow rates to the delivery distending media at low sensing flow rates. For example, according to the method embodiment shown schematically in FIG. 8, the method may comprise a timer reset step 810 for resetting a timer (that may be provided as a timer chip as part of the controller 101) prior to the initiation of pressure detection and/or conditional flow rate adjustment (step 610) and distending media delivery regulation (step 620). As shown in FIG. 8, the detecting and/or conditionally adjusting step 630 may comprise several subroutines for time-filtering pressure detection so as to avoid inappropriate shifts is distending media flow rate in response to momentary and/or transitory shifts in the detected pressure. According to one method embodiment, the detecting and/or conditionally adjusting step 630 may comprise steps for adjusting the flow rate from a sensing flow rate to an insufflating flow rate if the detected pressure rises above the low pressure transition point for a time period exceeding the time limit. However, in most cases the method embodiment may comprise time filter steps 831-834 for adjusting the flow rate from the insufflating flow rate to the sensing flow rate if the detected pressure falls below the high pressure transition point 402 for a time period 510 exceeding the time limit (see FIG. 5). For example, in step 831 the method may shift from sensing flow rate to insufflating flow rate if the detected pressure exceeds the low pressure transition point 401 for even a moment. Furthermore, step 832 may comprise starting the timer (counting down from the programmed time limit) when the detected pressure first falls below the high pressure transition point 402. According to steps 833 and 834, the method may then comprise adjusting from an insufflating flow rate to a sensing flow rate (see step 834) if the detected pressure falls below the high pressure transition point 402 for an uninterrupted time period exceeding the time limit 510. Electronically-performed embodiments of this method embodiment may also comprise an electronic feedback loop 650 for restarting the process after a flow rate adjustment has been made.

Additional method embodiments of the present invention, as shown for example in FIG. 9, may comprise a method for adaptively and/or automatically determining the low and high pressure transition points 401, 402 and/or the time limit 510 based upon historical pressure data that may be collected over time and stored in a memory device 108 (which may be in communication with the controller 101 in system 100 embodiments of the present invention). Thus, such adaptive methods may comprise steps for storing data comprising a plurality of detected pressure profiles corresponding to a plurality of insufflating procedures in a "pressure stability checker memory" (as shown generally in step 932). Such methods may also comprise steps for defining a time limit 510, a low pressure transition point 401, and a high pressure transition point 402, at least partially based on the stored data. According to some embodiments, the high pressure transition point 402 may be defined dynamically, such that the memory 108 may store a sample of immediately preceding pressure determinations and determine if subsequent measurements are within a defined range with respect to the preceding measurements (as shown generally in step 933). In some embodiments, the low pressure transition point 401 may be programmed within the controller 101 such that as the detected pressure exceeds the low pressure transition point 401, the controller 101 may initiate the adaptive portion of the method. However, in some embodiments, the adaptive portion of the method may include defining dynamic low pressure transition points 401 as well. Thus, the detecting and/or conditionally adjusting step 630 may comprise adjusting the flow rate from a sensing flow rate to an insufflating flow rate if the detected pressure rises above the dynamic low pressure transition point for a time period exceeding the time limit and/or adjusting the flow rate from the insufflating flow rate to the sensing flow rate if the detected pressure falls below the dynamic high pressure transition point for a time period exceeding the time limit (as shown generally in steps 931, 934).

In addition to providing systems and methods, the present invention also provides computer program products for performing the operations described above. The computer program products have a computer readable storage medium having computer readable program code means embodied in the medium. With reference to FIG. 1, the computer readable storage medium may be included as part of the controller 101 and/or memory device 108 in communication with the valve assembly 103, and may implement the computer readable program code means to perform the above discussed operations.

FIGS. 6-9 are non-limiting block diagrams, flowcharts and control flow illustrations of methods, systems and program products according to embodiments of the invention. It will be understood that each block or step of the block diagrams, flowcharts and control flow illustrations, and combinations of blocks in the block diagrams, flowcharts and control flow illustrations, can be implemented by computer program instructions. These computer program instructions may be loaded onto a computer (including, but not limited to the controller 101 in communication with the valve assembly 103 and/or other electro-pneumatic components of the insufflating system 100 described herein with respect to the embodiments of the present invention) or other programmable apparatus to produce a machine, such that the instructions which execute on the computer or other programmable apparatus form means for implementing the functions specified in the block diagrams, flowcharts or control flow block(s) or step(s). These computer program instructions may also be stored in a computer-readable memory that can direct a computer or other programmable apparatus to function in a particular manner, such that the instructions stored in the computer-readable memory may produce an article of manufacture including instruction means which can implement the function specified in the block diagrams, flowcharts or control flow block(s) or step(s). The computer program instructions may also be loaded onto a computer or other programmable apparatus, among other things, to cause a series of operational steps to be performed on the computer or other programmable apparatus. This may produce a computer implemented process such that the instructions which execute on the computer or other programmable apparatus provide steps for implementing the functions specified in the block diagrams, flowcharts or control flow block(s) or step(s).

Accordingly, blocks or steps of the block diagrams, flowcharts or control flow illustrations support, among other things, combinations of means for performing the specified functions, combinations of steps for performing the specified functions and program instruction means for performing the specified functions. It will also be understood that each block or step of the block diagrams, flowcharts or control flow illustrations, and combinations thereof, can be implemented by special purpose hardware-based computer systems which perform the specified functions or steps, or combinations of special purpose hardware and computer instructions.

Other modifications and other embodiments of the invention set forth herein will come to mind to one skilled in the art to which this invention pertains having the benefit of the teachings presented in the foregoing descriptions and on the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Further, throughout the description, where compositions are described as having, including, or comprising specific components, or where processes systems or methods are described as having, including, or comprising specific steps, it is contemplated that compositions or the present invention may also consist essentially or, or consist of the recited components, and that the processes or methods of the present invention also consist essentially or consist of the recited steps. Further, it should be understood that the order of steps or order of performing certain actions are immaterial so long as the invention remains operable. Moreover, two or more steps or actions may be conducted simultaneously with respect to the invention disclosed herein.

What is claimed is:

1. An insufflating system adapted to be in fluid communication with a source of a distending media and an endoscopic device so as to deliver the distending media to the endoscopic device, the insufflating system comprising:
   a controller for detecting a pressure level within a lumen of the endoscopic device; and
   a valve assembly in communication with said controller and in fluid communication between the source of distending media and the endoscopic device for delivering the distending media to the endoscopic device and adjusting a flow rate of the distending media delivered to the endoscopic device in response to the detected pressure level and at least one predetermined pressure threshold so as to prevent excess supply and waste of the distending media, wherein the at least one pressure threshold comprises a low pressure transition point and a high pressure transition point, wherein said controller is adapted to automatically control said valve assembly to increase the flow rate from a sensing flow rate to an insufflating flow rate for directing distending media into an anatomical cavity with the endoscopic device if the detected pressure level rises above the low pressure transition point, and wherein said controller is further adapted to automatically control said valve assembly to decrease the flow rate from the insufflating flow rate to a sensing flow rate if the detected pressure level falls below the high pressure transition point resulting from venting distending media to atmosphere with the endoscopic device.

2. An insufflating system according to claim 1, further comprising a disposable tubing set in fluid communication between an output of said valve assembly and the lumen of the endoscopic device.

3. An insufflating system according to claim 1, further comprising a filter device in fluid communication between an output of said valve assembly and a lumen of the endoscopic device, said filter device selected from a group consisting of:
   a biological filter, and
   a hydrophobic filter,
   so as to prevent passage of a pathogen from the endoscopic device to said valve assembly.

4. An insufflating system according to claim 1, further comprising a user interface, in communication with said controller and said valve assembly, for receiving a user input.

5. An insufflating system according to claim 4, wherein the user input comprises the at least one pressure threshold.

6. An insufflating system according to claim 4, wherein the user interface comprises a display for displaying data selected from the group consisting of:
   a volume of distending media delivered to the endoscopic device;
   a volume of distending media remaining in the distending media source;
   the user input; and
   combinations thereof.

7. An insufflating system according to claim 1, wherein the insufflating flow rate is between about 1 and 20 liters per minute, and wherein the sensing flow rate is between about 0.05 and 0.5 liters per minute.

8. An insufflating system according to claim 1, wherein the insufflating flow rate is between about 1 and 20 liters per minute, and wherein the sensing flow rate is between about 0.05 and 0.5 liters per minute.

9. An insufflating system according to claim 1, wherein said controller comprises a programmed time limit and wherein said controller is adapted to control said valve assembly to increase the flow rate from a sensing flow rate to an insufflating flow rate when the detected pressure rises above the low pressure transition point for a time period exceeding the time threshold and wherein said controller is further adapted to control said valve assembly decrease the flow rate from the insufflating flow rate to the sensing flow rate when the detected pressure falls below the high pressure transition point for a time period exceeding the time limit.

10. An insufflating system according to claim 1, further comprising a memory device in communication with said controller for storing data comprising detected pressures for a plurality of insufflating procedures and wherein the controller is further adapted to automatically define a time limit, a low pressure transition point, and a high pressure transition point, at least partially based on the stored data, and wherein said controller is adapted to control said valve assembly to increase the flow rate from a sensing flow rate to an insufflating flow rate if the detected pressure rises above the low pressure transition point for a time period exceeding the time limit and wherein said controller is further adapted to control said valve assembly decrease the flow rate from the insufflating flow rate to the sensing flow rate if the detected pressure falls below the high pressure transition point for a time period exceeding the time limit.

11. An insufflating system according to claim 1, wherein said controller comprises a pressure transducer.

12. An insufflating system according to claim 1, wherein said valve assembly comprises an electro-pneumatic valve.

13. An insufflating system according to claim 1, wherein the distending media is selected from the group consisting of:
   carbon dioxide;
   anti-spasmodic gaseous media;
   relaxant gaseous media; and
   combinations thereof.

14. An insufflating system according to claim 1, wherein said controller is adapted to automatically control said valve assembly to adjust the flow rate of the distending media delivered to the endoscopic device in response to a detected pressure level that is indicative of opening and closing of a valve associated with the endoscopic device for venting distending media to atmosphere.

15. An insufflating system according to claim 14, wherein said controller is adapted to automatically control said valve assembly to increase the flow rate to an insufflating flow rate if the valve associated with the endoscopic device is closed, and wherein said controller is further adapted to automatically control said valve assembly to decrease the flow rate to a sensing flow rate if the valve associated with the endoscopic device is open.

16. A method for delivering distending media to an endoscopic device in fluid communication with a source of a distending media, the method comprising:
   detecting a pressure level within a lumen of the endoscopic device;
   delivering the distending media to the endoscopic device
   automatically adjusting a flow rate of the distending media delivered to the endoscopic device in response to the detected pressure level and at least one pressure threshold so as to prevent excess supply and waste of the distending media, wherein the at least one pressure threshold comprises a low pressure transition point and a high pressure transition point, and wherein the adjusting step further comprises:
      increasing the flow rate from a sensing flow rate to an insufflating flow rate for directing distending media into an anatomical cavity with the endoscopic device if the detected pressure level rises above the low pressure transition point; and
      decreasing the flow rate from the insufflating flow rate to a sensing flow rate if the detected pressure level falls below the high pressure transition point resulting from venting distending media to atmosphere with the endoscopic device.

17. A method according to claim 16, further comprising filtering a fluid pathway between the source and the endoscopic device so as to prevent passage of a pathogen from the endoscopic device to the source of the distending media.

18. A method according to claim 16, further comprising receiving a user input for controlling the adjusting step.

19. A method according to claim 18, wherein the user input comprises the at least one pressure threshold.

20. A method according to claim 16, wherein the insufflating flow rate is between about 1 and 20 liters per minute, and wherein the sensing flow rate is between about 0.05 and 0.5 liters per minute.

21. A method according to claim 16, wherein the insufflating flow rate is between about 1 and 20 liters per minute, and wherein the sensing flow rate is between about 0.05 and 0.5 liters per minute.

22. A method according to claim 16, further comprising providing a programmed time limit and wherein the adjusting step further comprises:
   increasing the flow rate from a sensing flow rate to an insufflating flow rate if the detected pressure rises above the low pressure transition point for a time period exceeding the time limit; and
   decreasing the delivery parameter from the insufflating flow rate to the sensing flow rate if the detected pressure falls below the high pressure transition point for a time period exceeding the time limit.

23. A method according to claim 16, further comprising:
   storing data comprising a plurality of detected pressure profiles corresponding to a plurality of insufflating procedures;
   defining a time limit, a low pressure transition point, and a high pressure transition point, at least partially based on the stored data; and wherein the adjusting step further comprises:
      increasing the flow rate from a sensing flow rate to an insufflating flow rate if the detected pressure rises above the low pressure transition point for a time period exceeding the time limit; and
      decreasing the flow rate from the insufflating flow rate to the sensing flow rate if the detected pressure falls below the high pressure transition point for a time period exceeding the time limit.

24. A method according to claim 16, further comprising initially setting a flow rate of the distending media delivered to the endoscopic device to a sensing flow rate, and regulating the delivery of the distending media to the endoscopic device at a set flow rate.

25. A method according to claim 24, wherein said adjusting step comprises:
   increasing the set flow rate to an insufflating flow rate if the detected pressure level rises above the low pressure transition point; and
   decreasing the set flow rate to a sensing flow rate if the detected pressure level falls below the high pressure transition point.

26. A method according to claim 16, wherein said adjusting step comprises automatically adjusting the flow rate of the distending media delivered to the endoscopic device in response to a detected pressure level that is indicative of opening and closing of a valve associated with the endoscopic device for venting distending media to atmosphere.

27. A method according to claim 26, wherein said adjusting step further comprises:
   increasing the flow rate to an insufflating flow rate if the valve associated with the endoscopic device is closed; and
   decreasing the flow rate to a sensing flow rate if the valve associated with the endoscopic device is open.

* * * * *

UNITED STATES PATENT AND TRADEMARK OFFICE
CERTIFICATE OF CORRECTION

| | |
|---|---|
| PATENT NO. | : 7,806,850 B2 |
| APPLICATION NO. | : 11/257229 |
| DATED | : October 5, 2010 |
| INVENTOR(S) | : Williams, Jr. et al. |

It is certified that error appears in the above-identified patent and that said Letters Patent is hereby corrected as shown below:

<u>Column 9,</u>
Line 7, "insulating" should read --insufflating--.

Signed and Sealed this
Twenty-second Day of November, 2011

David J. Kappos
*Director of the United States Patent and Trademark Office*